(12) United States Patent
Astilla et al.

(10) Patent No.: US 11,517,455 B2
(45) Date of Patent: Dec. 6, 2022

(54) SUCTION LANYARD PROSTHESIS SUSPENSION SYSTEM

(71) Applicants: Michael Joseph Astilla, Durham, NC (US); Brian Gold, Durham, NC (US)

(72) Inventors: Michael Joseph Astilla, Durham, NC (US); Brian Gold, Durham, NC (US)

(*) Notice: Subject to any disclaimer, the term of this patent is extended or adjusted under 35 U.S.C. 154(b) by 0 days.

(21) Appl. No.: 16/890,405

(22) Filed: Jun. 2, 2020

(65) Prior Publication Data
US 2021/0353440 A1    Nov. 18, 2021

Related U.S. Application Data

(60) Provisional application No. 63/024,857, filed on May 14, 2020.

(51) Int. Cl.
*A61F 2/80* (2006.01)
*A61F 2/50* (2006.01)
*A61F 2/78* (2006.01)

(52) U.S. Cl.
CPC ........ *A61F 2/80* (2013.01); *A61F 2002/5007* (2013.01); *A61F 2002/5053* (2013.01); *A61F 2002/7856* (2013.01); *A61F 2002/7868* (2013.01); *A61F 2002/805* (2013.01)

(58) Field of Classification Search
CPC ................ A61F 2/80; A61F 2002/7856; A61F 2002/7868; A61F 2002/802; A61F 2002/805; A61F 2002/807
See application file for complete search history.

(56) References Cited

U.S. PATENT DOCUMENTS

| 6,797,008 B1* | 9/2004 | Arbogast ................. A61F 2/78 623/34 |
| 7,727,284 B2* | 6/2010 | Warila ..................... A61F 2/78 623/36 |
| 7,883,547 B2* | 2/2011 | Mantelmacher .......... A61F 2/78 623/34 |
| 9,492,292 B2* | 11/2016 | Mantelmacher .......... A61F 2/76 |
| 2019/0083285 A1* | 3/2019 | Hillmann ............. A61F 2/7812 |

* cited by examiner

*Primary Examiner* — Bruce E Snow
(74) *Attorney, Agent, or Firm* — Taylor English Duma

(57) ABSTRACT

An apparatus for suspending a prosthesis from a residual limb comprises a tubular liner adapted to receive the residual limb. A lanyard is secured at one end to the distal end of the liner. A hollow prosthetic socket defines a well configured to receive the residual limb and includes a socket seal disposed at the distal end of the socket. An upper surface of the socket seal defines a recess opening to the exterior of the socket through a side wall. A sealing element disposed along the length of the lanyard is configured to engage within the passage. The free end of the lanyard is pulled through passage such that the sealing element sealingly engages within the passage for preventing fluid communication through the passage. The liner at least partially contacts the interior surface of the socket for providing a fluid seal and creating negative pressure within the socket.

13 Claims, 20 Drawing Sheets

SUCTION LANYARD PROSTHESIS SUSPENSION SYSTEM

CROSS-REFERENCE TO RELATED APPLICATIONS

This application is related to U.S. provisional application No. 63/024,857, filed May 14, 2020, entitled "Suction Lanyard Prosthesis Suspension System", naming Michael Astilla and Brian Gold as the inventors. The contents of the provisional application are incorporated herein by reference in their entirety, and the benefit of the filing date of the provisional application is hereby claimed for all purposes that are legally served by such claim for the benefit of the filing date.

BACKGROUND

An apparatus, system and method for suspending a prosthesis from a limb are described and, more particularly, a suspending apparatus, system and method using a combination of suspension alternatives for securing the prosthesis to the limb.

A prosthesis replaces an amputated or missing portion of a limb and helps restore the ability to use that limb. For example, a typical prosthetic assembly for a lower leg includes a custom fitted thermoplastic socket, an artificial foot and a weight-bearing shaft between the socket and the foot. An amputee dons the prosthetic assembly by inserting part of their remaining limb, the residual limb or "residuum", into the socket to connect the prosthetic assembly to the body. An inner liner or sheath may also be worn on the residual limb like a sock, conforming to the residual limb. The typical liner is formed from a flexible, thermoplastic material, which cushions and protects the residual limb as well as providing a snug fit for an air-tight seal between the residual limb and the socket.

Several alternatives are available for suspending the prosthesis from the residual limb, which are generally characterized as mechanical suspension systems and negative pressure, or vacuum, suspension systems. One type of mechanical suspension system includes a lanyard attached at one end to a distal end of the liner. A free end of the lanyard is pulled through an opening in a distal end of the socket and fastened to the outer surface of the socket. While this arrangement is simple and effective for suspending the prosthesis, the lanyard-type mechanical suspension system provides only a single point of support on a residual limb and allows the prosthesis to rotate on the limb.

Negative pressure suspension systems secure the prosthesis by suction formed by sealing contact between the residual limb or the liner and an inner surface of the socket. The suction is created by the tight fit of the residual limb in the socket. A vacuum pump integral to the socket may also work in combination with the tight fit. Unfortunately, a prosthetic assembly including negative pressure suspension can be difficult to don. For example, the user and clinician must ensure the residuum is fully seated into the distal end of the socket; however, there is no feedback indicating when the socket is properly and completely donned. Negative pressure suspension systems also do not enable the user to place the residuum and associated tissue under tension during donning. Further, most amputees experience some changes in the fluid volume of the residual limb throughout the day. Volume changes may cause the socket to fit improperly, making the prosthesis uncomfortable or causing the device to loosen or fall off when there is loss of significant volume from the residual limb.

For the foregoing reasons, there is a need for an improved apparatus, system and method for suspending a prosthesis. Ideally, the new suspension apparatus and system should provide the benefits of both mechanical suspension systems and negative pressure systems for securing the residual limb to the prosthesis.

SUMMARY

An apparatus is provided for suspending a prosthesis from a residual limb having a distal end. The suspending apparatus comprises a tubular flexible resilient liner having a closed distal end. The liner is adapted to receive at least a portion of the residual limb including the distal end of the residual limb. A lanyard is secured at one end to the distal end of the liner. A rigid hollow prosthetic socket has an open proximal end, a closed distal end, and interior side surfaces defining a well configured to receive the residual limb. The prosthetic socket includes a socket seal disposed at the distal end of the socket. The socket seal comprises a body having an upper surface, a lower surface and a side wall interconnecting the upper surface and the lower surface, the upper surface defining a recess opening to the exterior of the socket through the side wall for forming a passage for passing the free end of the lanyard. A sealing element is disposed along the length of the lanyard, the sealing element configured to engage the socket seal within the passage. The free end of the lanyard is pulled through the passage such that the sealing element sealingly engages the socket seal within the passage for preventing fluid communication through the passage between the interior of the socket and exterior of the socket. The distal end of the residual limb covered by the liner fits snugly within the socket such that the liner at least partially contacts the interior side surfaces of the socket for providing a fluid seal to the socket and creating negative pressure within the socket.

In one aspect, the liner comprises a mechanical locking pin configured to engage the one end of the lanyard, wherein the locking pin comprises a threaded bolt and nut combination.

In another aspect, the upper surface of the body of the socket seal is concave and may comprise an elastomer. Moreover, the passage may be rectilinear in cross-section, and the sealing element a flexible resilient wedge. The socket seal may be substantially cylindrical and the side wall include an integral radially extending annular flange integrally molded with the socket, or the sidewall may define a circumferential groove.

The suspending apparatus may further comprise a one-way valve disposed in a second fluid passage extending through the socket allowing fluid flow only from the interior of the socket to the exterior of the socket and preventing backflow of fluid. As the socket is donned the residual limb and the liner force air from the interior of the socket through the one-way valve to the exterior of the socket for creating negative pressure between the residual limb and the interior of the socket.

The suspending apparatus may further comprise a locking mechanism disposed on the exterior surface of the socket, wherein the locking mechanism secures the free end of the lanyard and an O-ring seal on the interior side surface adjacent the proximal end of the socket.

In another embodiment, a prosthesis for a residual limb comprises a prosthetic socket having an open proximal end, a closed distal end and interior side surfaces defining a well configured to receive the residual limb. A liner is configured for receiving the residual limb and providing total contact between the residual limb the interior side surfaces of the prosthetic socket. A lanyard depends from a distal end of the liner and includes an integral sealing element. A socket seal at the distal end of the socket has a proximal upper surface, a distal lower surface, and a side wall interconnecting the upper surface and the lower surface. The upper surface defines a recess opening to the exterior of the socket through the side wall for forming a passage for passing the free end of the lanyard such that the sealing element fluidically seals the passage within the socket seal. A rigid assembly is configured to attach to the socket for use as an artificial limb.

A method is provided for making a prosthetic limb socket for an apparatus for suspending a prosthesis to a residual limb. The method of making the socket comprises the steps of providing a socket model having a distal end and affixing a removable mold dummy to the distal end of the socket model. A prosthetic socket is molded over the socket model and around the removable dummy and the socket model and the dummy are subsequently removed from the prosthetic socket. The method further comprises the step of inserting a socket seal at the distal end of the socket, the socket seal comprising a body having an upper surface, a lower surface and a side wall interconnecting the upper surface and the lower surface, the upper surface defining a recess opening to the exterior of the socket seal forming a passageway through the socket seal.

The method of making the suspending apparatus may further comprise the steps of providing a locking mechanism on the exterior surface of the socket, or securing a prosthetic limb to the distal end of the socket.

A method for suspending a prosthesis from a residual limb having a distal end comprises the steps of providing a tubular flexible resilient liner having a closed distal end, the liner including a lanyard having an integral sealing element and an end secured to the distal end of the liner. The user inserts at least a portion of the residual limb including the distal end of the residual limb into the liner. A rigid hollow prosthetic socket is provided having an open proximal end, a closed distal end, and interior side surfaces defining a well configured to receive the residual limb. The prosthetic socket includes a socket seal disposed at the distal end of the socket, the socket seal comprising a body having an upper surface, a lower surface, and a side wall interconnecting the upper surface and the lower surface, wherein the upper surface defines a recess opening to the exterior of the socket through the side wall for forming a passage. The user pulls a free end of the lanyard through the passage for elongating the liner and the residual limb, and advances the liner and the elongated residual limb into the socket until the distal end of the residual limb seats against the upper surface of the socket seal and the sealing element engages in the passage within the socket seal for preventing fluid communication through the passage between the interior of the socket and exterior of the socket.

The prosthesis suspending method may further comprise the step of providing a locking mechanism disposed on the exterior surface of the socket, and securing the free end of the lanyard to the locking mechanism.

BRIEF DESCRIPTION OF THE DRAWINGS

For a more complete understanding of the apparatus, system and method for suspending a prosthesis, reference should now be had to the embodiments shown in the accompanying drawings and described below. In the drawings.

DETAILED DESCRIPTION

Certain terminology is used herein for convenience only and is not to be taken as a limiting. For example, words such as "upper," "lower," "left," "right," "horizontal," "vertical," "upward," "downward," "top" and "bottom" merely describe the configurations shown in the FIGs. Indeed, the components may be oriented in any direction and the terminology, therefore, should be understood as encompassing such variations unless specified otherwise. The words "interior" and "exterior" refer to directions toward and away from, respectively, the geometric center of the core and designated parts thereof. The terminology includes the words specifically mentioned above, derivatives thereof and words of similar import.

Figure 1:
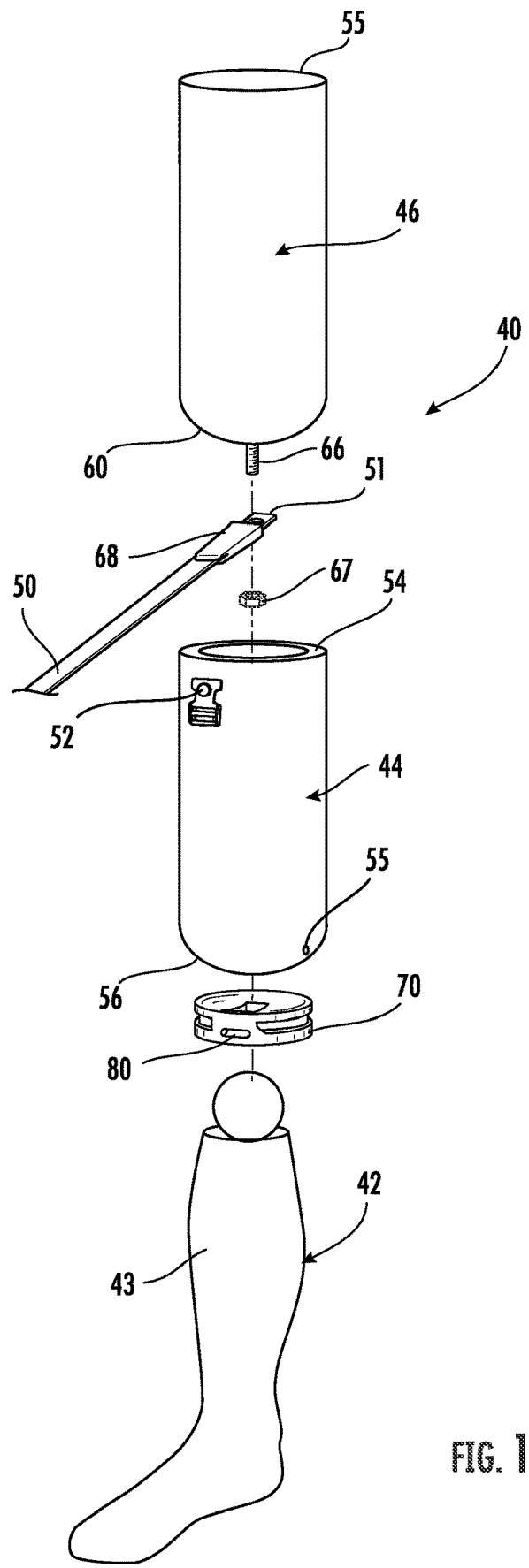
FIG. 1 is a front exploded perspective view of an embodiment of an apparatus for suspending a lower leg prosthesis including the lower leg prosthesis.
Figure 2:
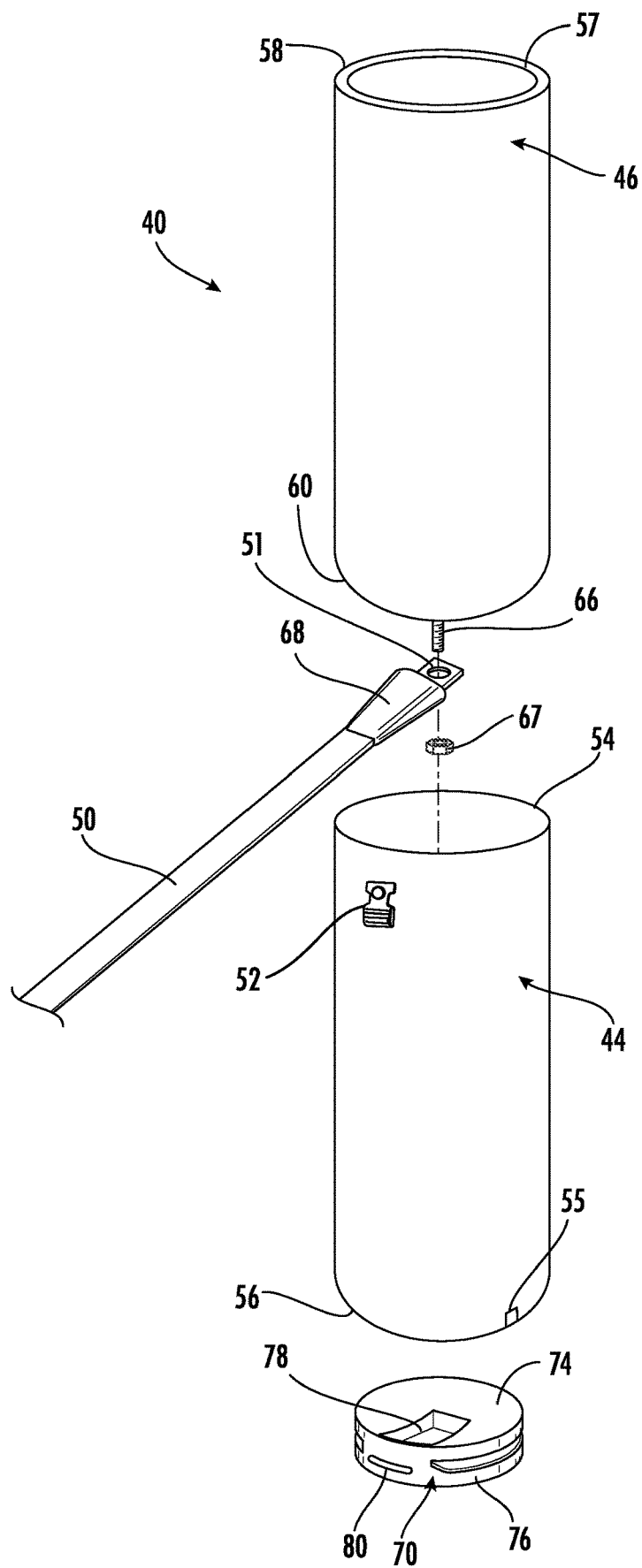
FIG. 2 is a front exploded perspective view of the apparatus for suspending a lower leg prosthesis as shown in FIG. 1.

Referring now to the drawings, wherein like reference numerals designate corresponding or similar elements throughout the several views, an embodiment of an apparatus for suspending a prosthesis from a residual is limb is shown FIGS. 1 and 2 and generally designated at 40. In the embodiments shown, the prosthesis 42 is an above-the-knee prosthetic limb. The suspension apparatus 40 comprises a prosthetic socket 44 and a tubular liner 46, both configured to be placed over a residual limb 48. A lanyard 50 is fastened to the liner 46 as a part of a mechanical suspension assembly for securing the residual limb 48 within the socket 44. In use, the liner 46 provides a snug fit between the residual limb 48 and the inner surface of the socket 44, contacting the inner surface for yielding an air tight seal. Thus, the suspension apparatus 40 combines the mechanical suspension assembly with a second securing force of negative pressure suspension of the residual limb 48 in the socket 44. The configuration of the combined mechanical suspension and negative pressure suspension systems also allows the user to don the prosthesis 42 more easily by pulling the lanyard 50 for elongating the residual limb 48 while inserting the residual limb into the socket 44. As the residual limb 48 is pulled into the socket 44 by the lanyard 50, visual and audible confirmation that the prosthesis 42 is fully and properly donned is provided when the lanyard 50 reaches and is locked to a latch 52 positioned on the outer surface of the socket 44.

The prosthetic socket 44 comprises an elongated hollow generally cylindrical member having an open proximal end 54 and a closed distal end 56 and an inner surface defining an interior configured for receiving the residual limb 48. The proximal end 54 of the socket 44 may include a sealing mechanism (not shown), such as an O-ring, a gasket, or the like. The sealing mechanism is positioned proximally and, when the user dons the socket 44, is compressed between the liner 46 and the inner surface of the socket 44 to provide a closed system within the interior of the socket. The distal end 56 of the socket 44 is configured to be connected to a top end of a support member 43 of the prosthesis 42 in a conventional manner. The distal end 56 of the socket 44 may have a one-way air valve (not shown) in fluid communication with the interior of the socket. The one-way valve allows for the expulsion of air within the socket 44 as the socket is donned and prevents backflow, which helps to establish and maintain a negative pressure seal.

As is known in the art, the socket 44 is fabricated to accommodate various shapes and sizes based on patient-specific distal residuum anatomy. The socket 44 can be custom-made from a measured, digital, or hand formed model of a residuum. In one embodiment, the socket 44 may be vacuum formed from a substantially rigid material such as of a thermoplastic material or composite material. Those skilled in the art, however, will readily appreciate that other materials having suitable strength, flexibility, and durability characteristics may alternatively be used.

The prosthetic liner 46 comprises a flexible tubular sleeve having a proximal end 58 and a distal end 60. The liner 46 is formed from fabric, foams, gel materials, combinations thereof or other suitable material to provide cushioning for the residuum. As is known in the art, the liner 46 is configured to be worn over at least the portion of the residual limb 48 that is placed within the socket 44. In addition to providing for a negative pressure seal, the tight fitting liner 46 contacts and increases the coefficient of friction between the residual limb 48 and the inner surface of the socket 44, thereby ensuring a secure fit. A variety of suitable liner designs and materials are known in the art.

A threaded cylindrical locking pin 66 is provided at the distal end 60 of the liner 46. The locking pin 66 is integrated into the distal aspect of the liner 46 via mechanical or adhesive means such that the pin 66 projects distally along a central longitudinal axis of the liner 46.

The lanyard 50 is fastened on the pin 66 at the distal end 60 of the liner 46. One end of the lanyard 50 has an opening 51 configured to receive the threaded pin 66. The lanyard may be secured to the liner seal 62 by a nut 67 that threadably engages the locking pin 66. Other suitable connecting mechanisms may include, for example, loop and hook materials, vacuum systems, cohesion, threaded imbedded fixtures in a diaphragm, and the like. The lanyard 50 may include multiple access points to connect to the latch 52 to firmly secure the lanyard 50 to the socket 44. For example, the lanyard may have cooperating hook and loop surfaces for adjusting tension of the lanyard, or the latch 52 may be a conventional buckle and lanyard have longitudinally spaced holes for use with the buckle 52.

Figure 3:
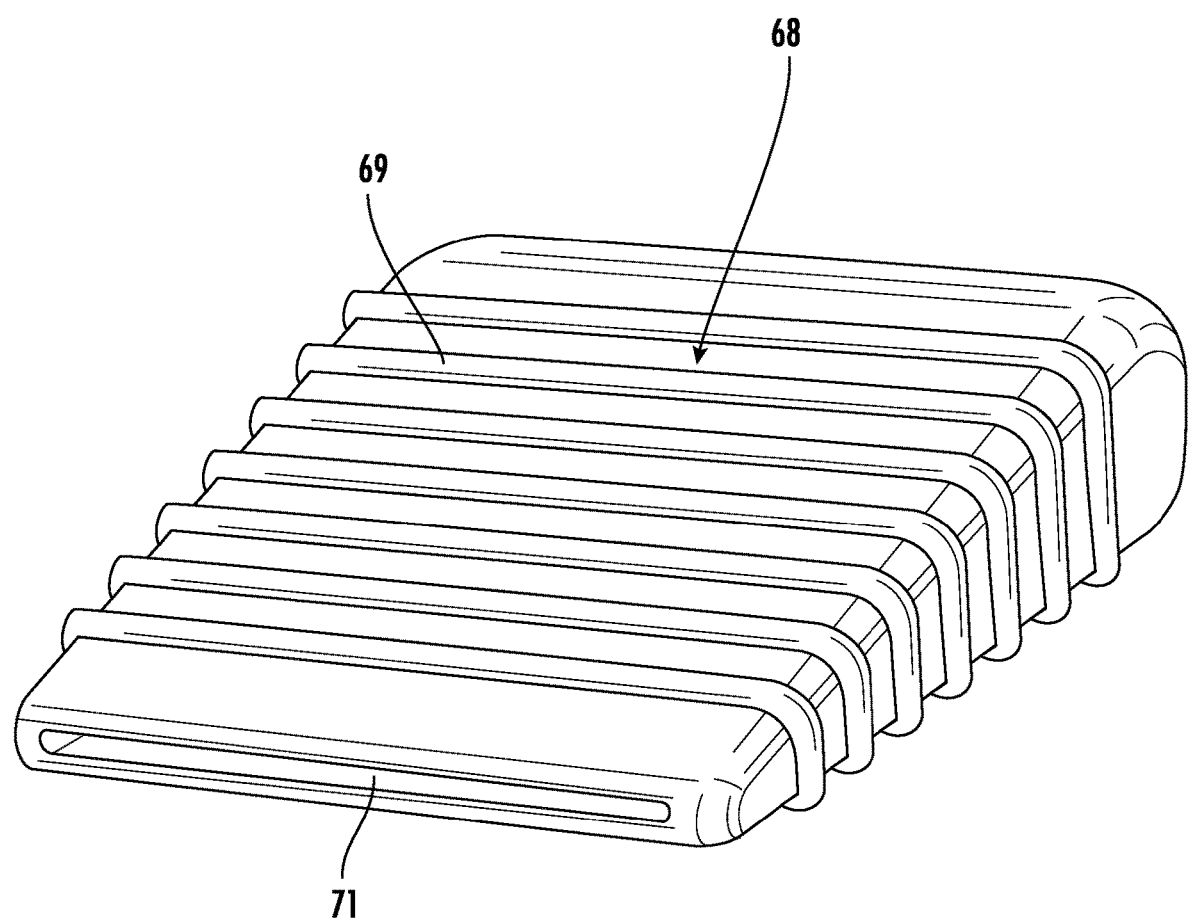
FIG. 3 is a front perspective view of an embodiment of a sealing element for use with the suspending apparatus as shown in FIG. 1.
Figure 4:
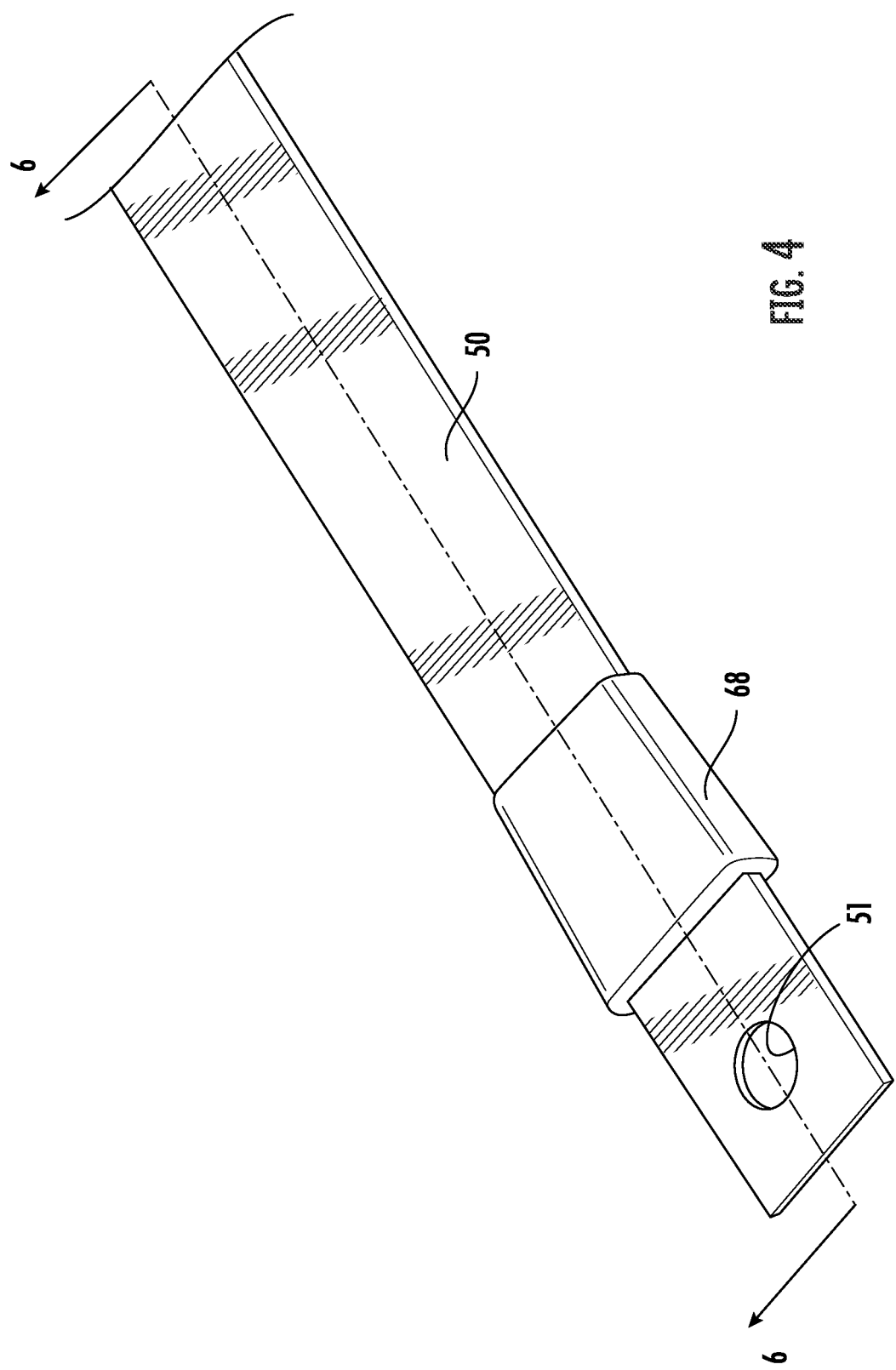
FIG. 4 is a top perspective partially cut-away view of an embodiment of a lanyard and another embodiment of the sealing element for use with the suspending apparatus as shown in FIG. 1.
Figure 5:
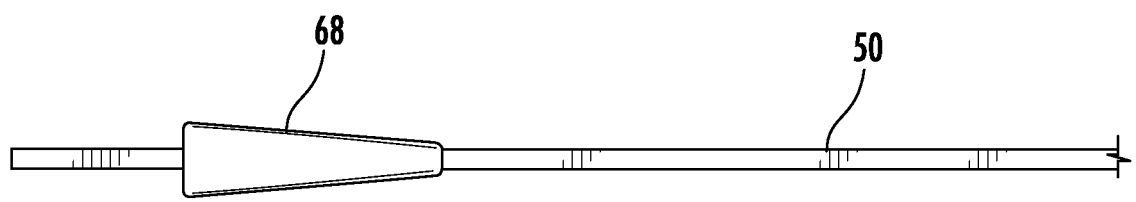
FIG. 5 is a side elevation view of the lanyard and the sealing element as shown in FIG. 4.
Figure 6:
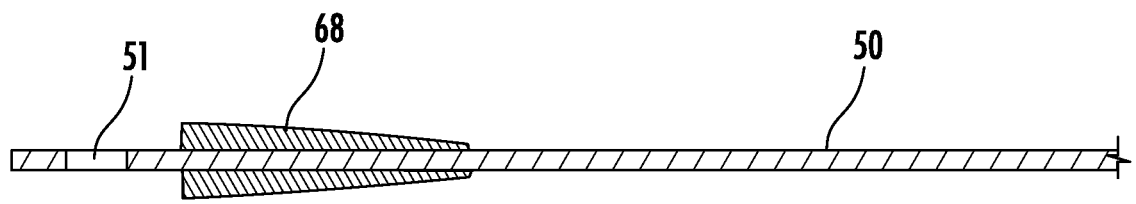
FIG. 6 is a longitudinal cross-section view of the lanyard and the sealing element taken along line 6-6 of FIG. 4.
Figure 7:
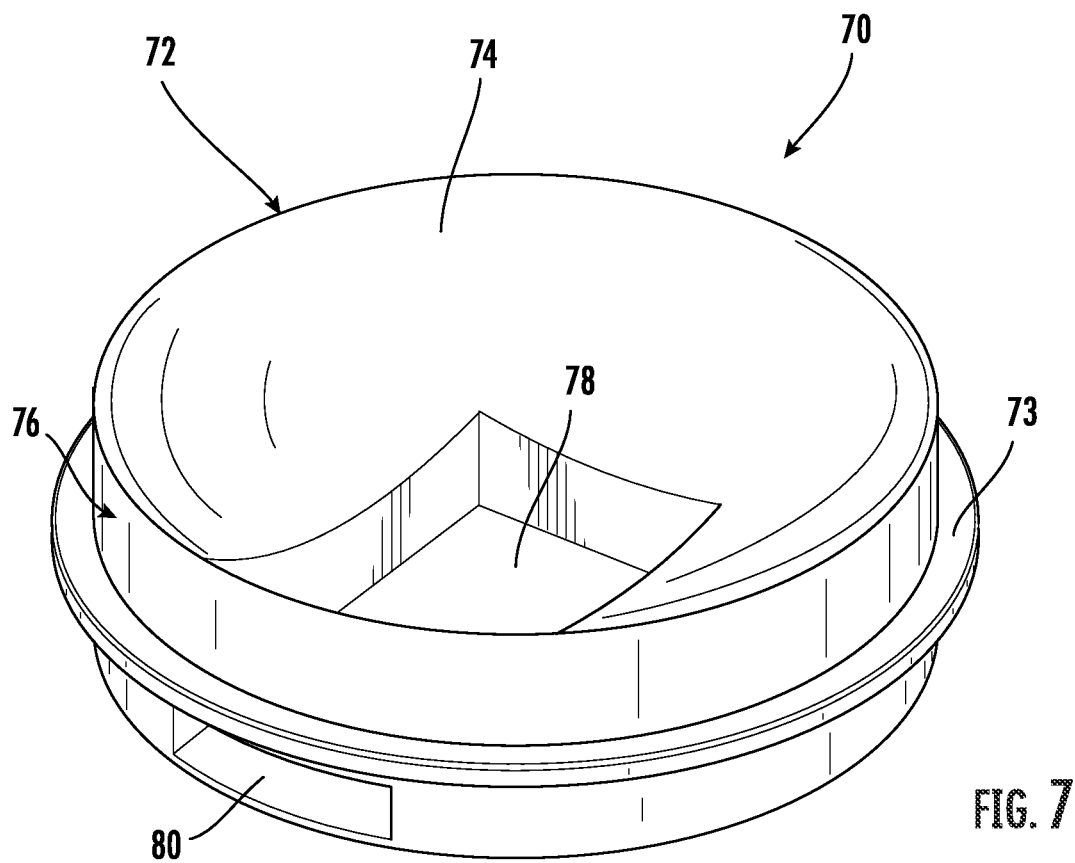
FIG. 7 is a top front perspective view of an embodiment of a socket seal for use with the suspending apparatus as shown in FIG. 1.
Figure 8:
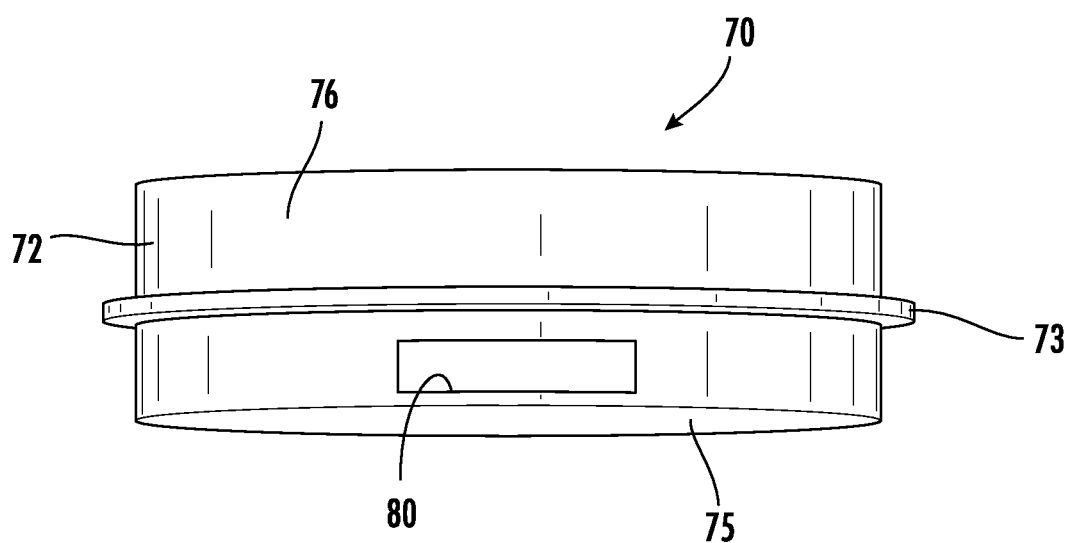
FIG. 8 is a front elevation view of the socket seal as shown in FIG. 7.
Figure 9:
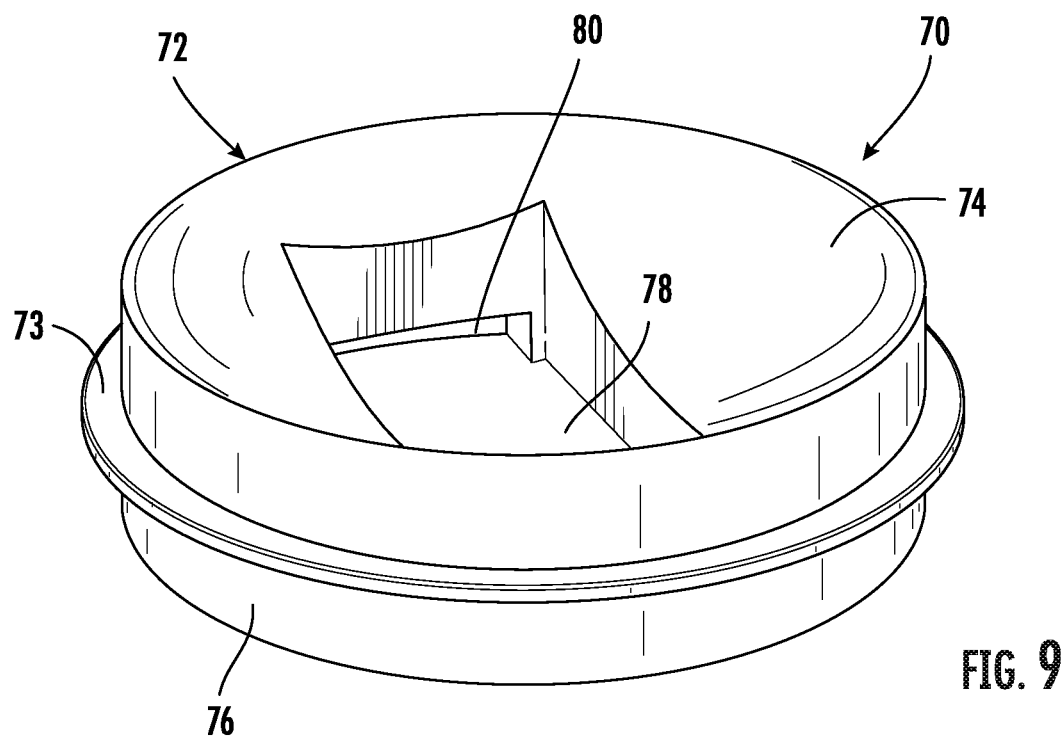
FIG. 9 is a top rear perspective view of the socket seal as shown in FIG. 7.
Figure 10:
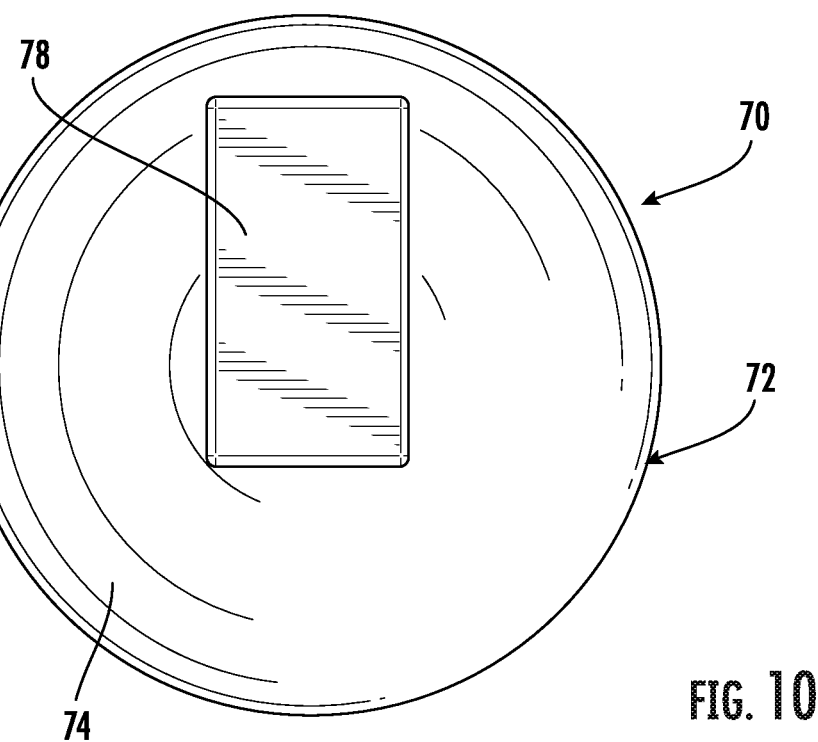
FIG. 10 is a top plan view of the socket seal as shown in FIG. 7.

A wedge-shaped plug 68 surrounds the lanyard 50 at an intermediate point along its length (FIGS. 4-6). As will be described below, the plug 68 is configured to seal the lanyard 50 in the socket seal to maintain negative pressure within the socket 44. An embodiment of the plug 68 shown in FIG. 3 may include transverse ribs for promoting sealing engagement in a socket seal 70, as will be described below.

Figure 11:
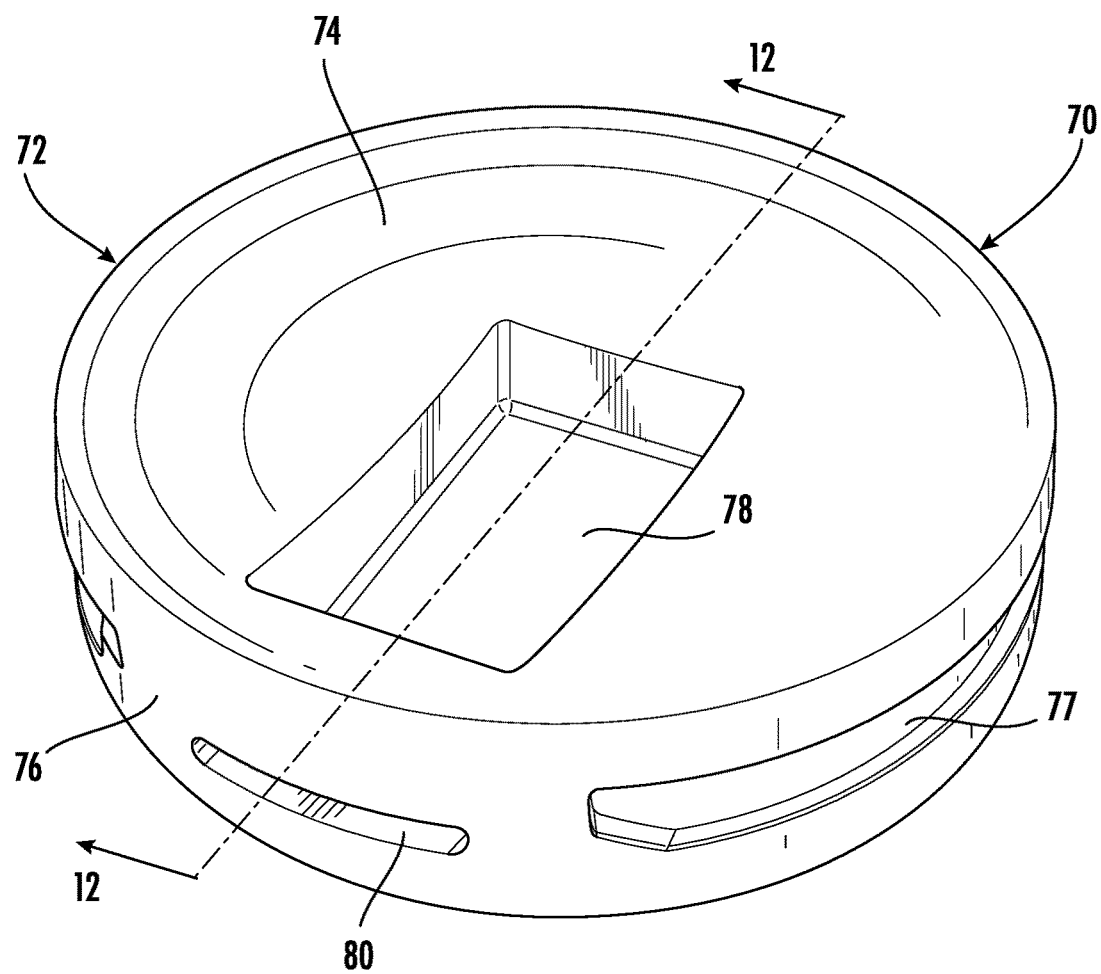
FIG. 11 is a top front perspective view of another embodiment of a socket seal for use with the suspending apparatus as shown in FIG. 1.
Figure 12:
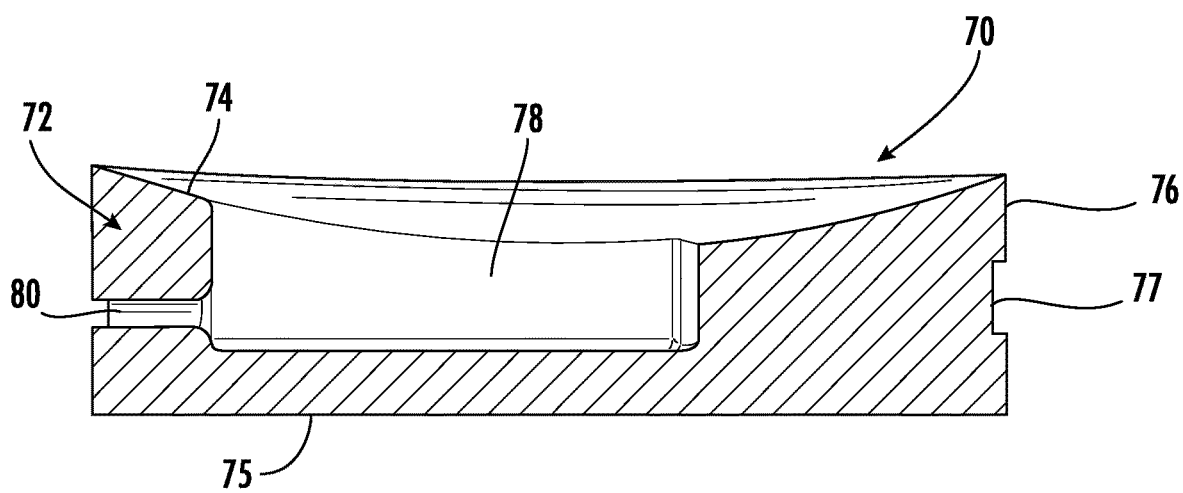
FIG. 12 is a cross-section view of the socket seal taken along line 12-12 of FIG. 11.

The socket seal 70 is mounted within the distal end 56 of the socket 44. Referring to FIGS. 7-12, the socket seal 70 comprises a circular disc-like body 72 formed from an elastomeric material. The body 72 of the socket seal 70 has a concave upper surface 74, a generally planar lower surface 75 and a sidewall 76 that extends between and interconnects the upper surface and the lower surface. The concave upper surface 74 of the socket seal 70 generally conforms to the distal portion of a residuum 48 providing a comfortable fit for the residual limb 48 within the socket 44. The elastomeric material of the body 72 of the socket seal 70 provides cushion and shock absorption when a user applies pressure during ambulation. The sidewall 76 is complementally configured to the inside surface of the socket 44 such that the socket seal 70 fits in sealing relationship within the socket. In one embodiment, the body 72 of the socket seal 70 has a radially extending annular flange (FIGS. 7-10). In another embodiment, the body 72 may define a circumferential groove around most of the periphery of the sidewall 76 (FIGS. 11 and 12).

Figure 13:
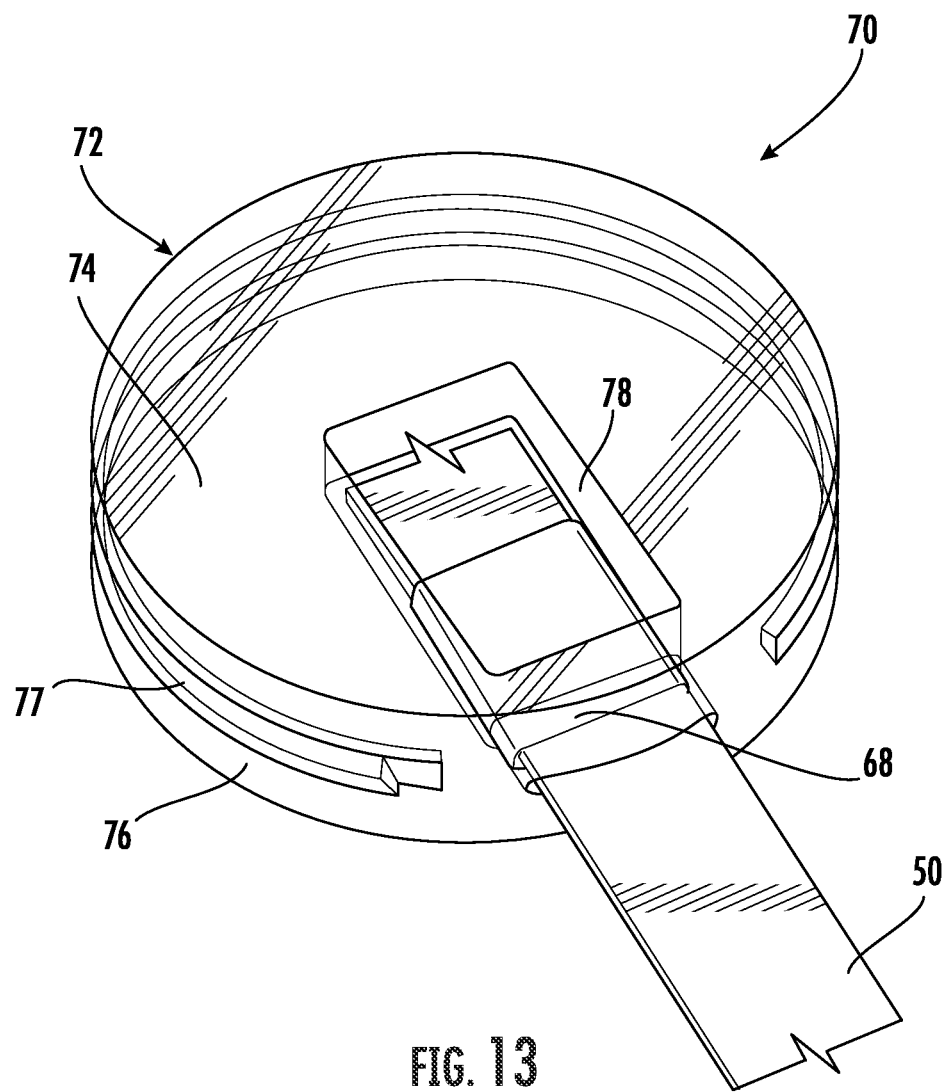
FIG. 13 is a top perspective view of the socket seal as shown in FIG. 11 including a cut-away portion of the lanyard and the sealing element as shown in FIG. 4.
Figure 14:
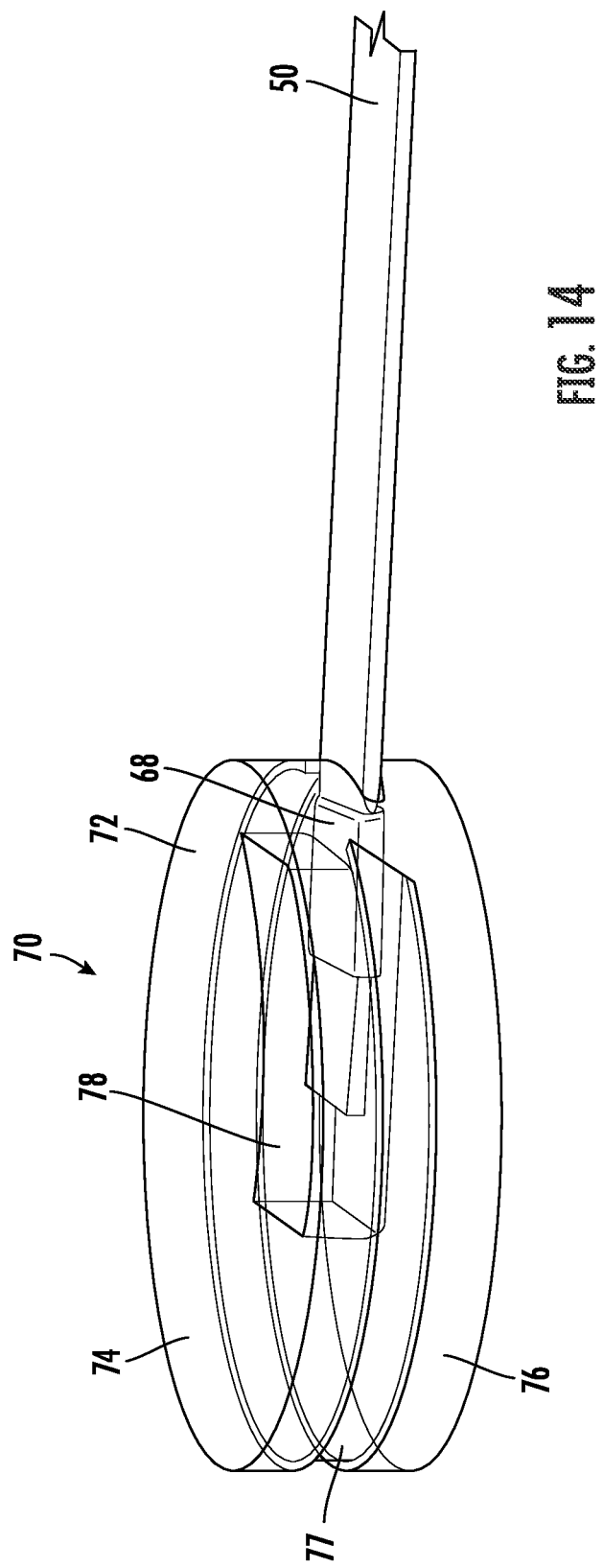
FIG. 14 is a side perspective view of the socket seal including the lanyard and the sealing element as shown in FIG. 13.
Figure 15:
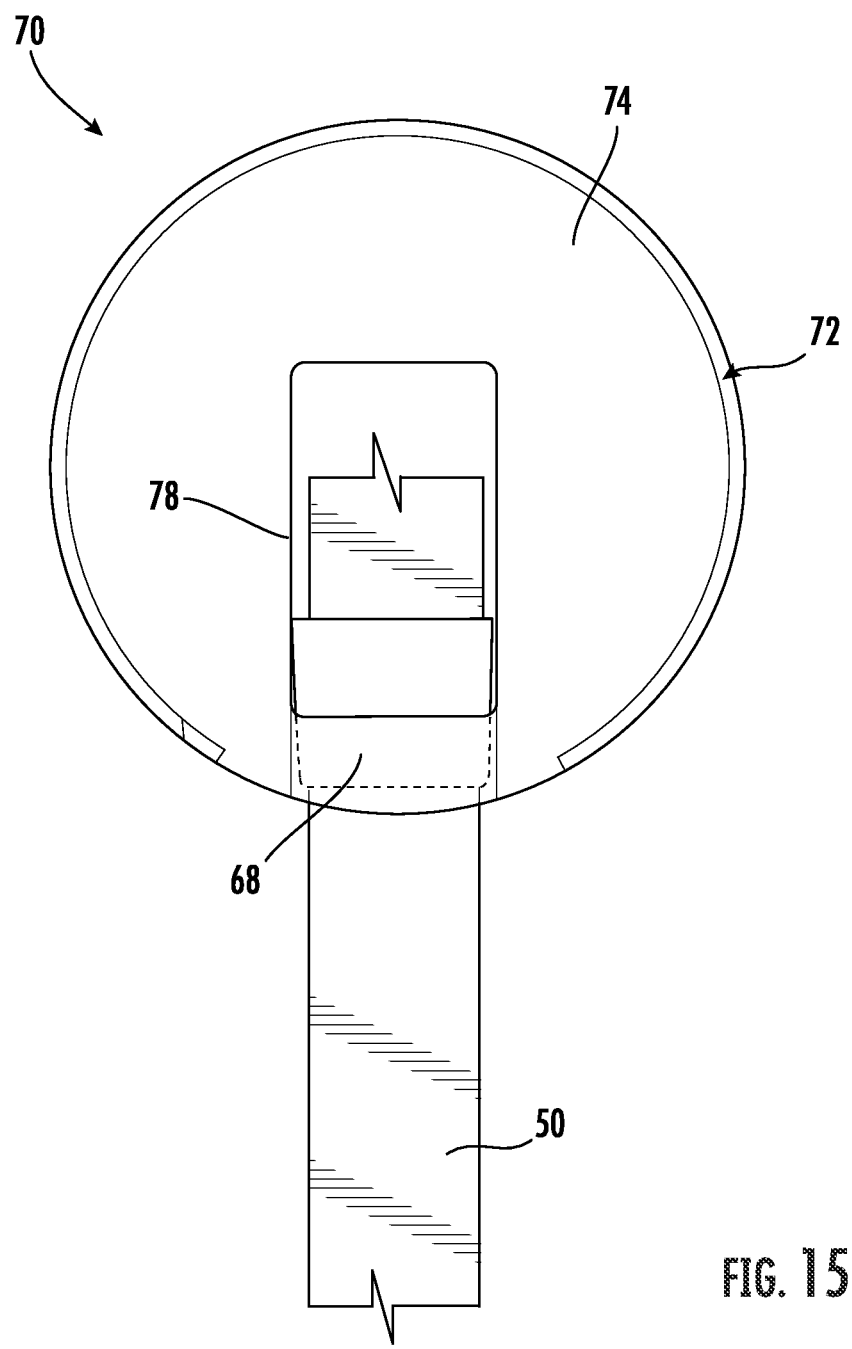
FIG. 15 is a top plan view of the socket seal including the lanyard and the sealing element as shown in FIG. 13.
Figure 16:
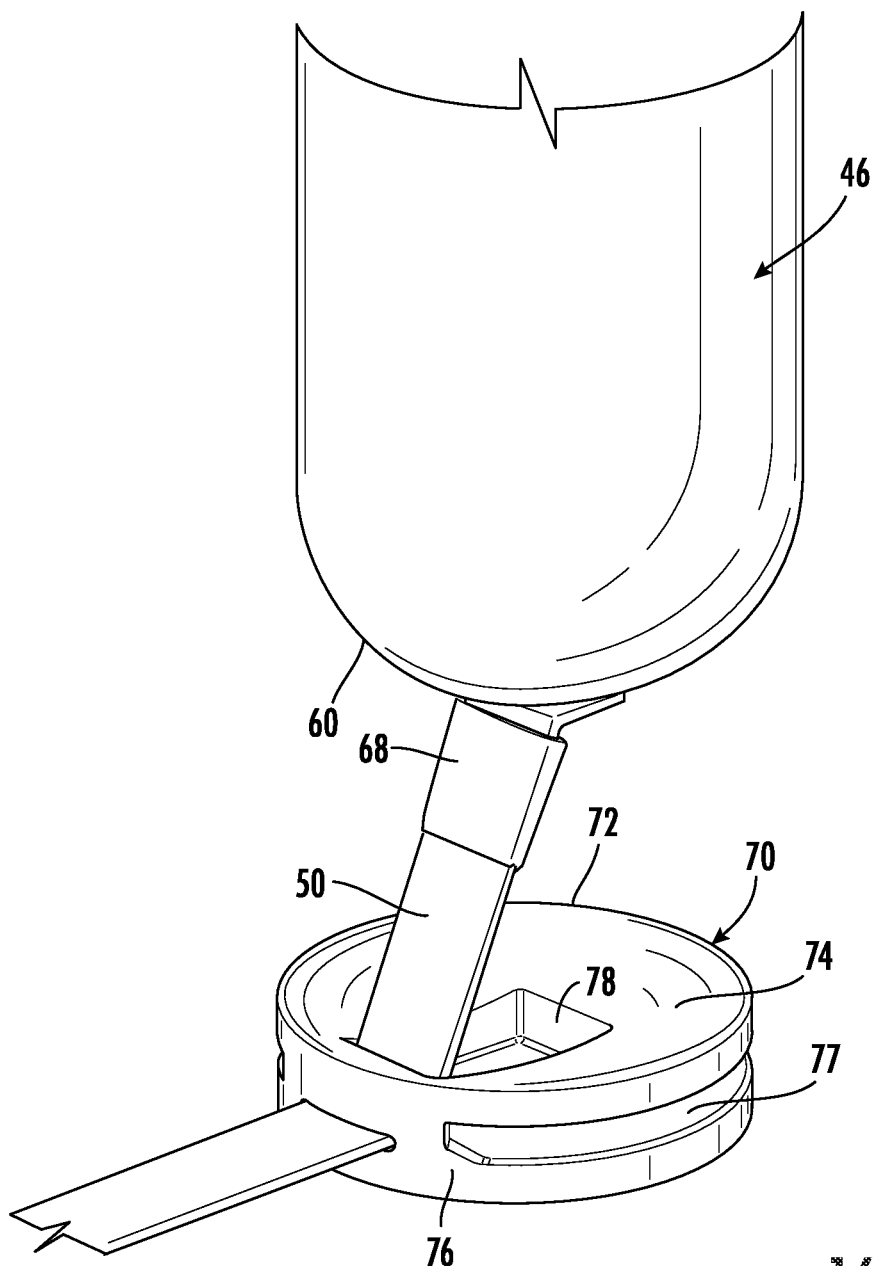
FIG. 16 is a front perspective view of the socket seal as shown in FIG. 11 including an embodiment of a liner with the lanyard and the sealing element as shown in FIG. 1.
Figure 17:
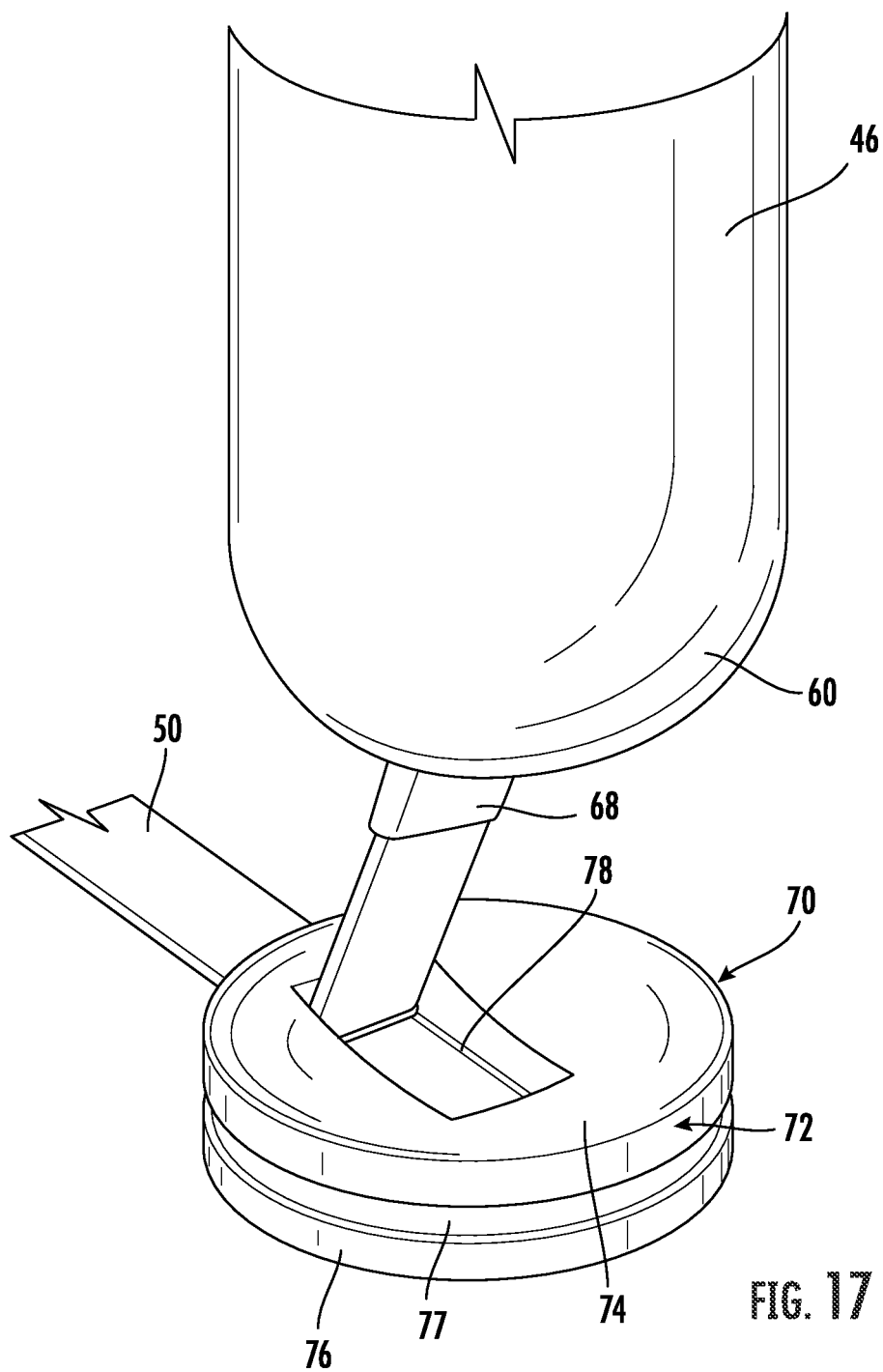
FIG. 17 is a rear perspective view of the socket seal and the liner with the lanyard and the sealing element as shown in FIG. 16.

The socket seal 70 defines a radial slot 78 extending outwardly from a central axis of the socket seal 72 and opening into the interior space defined by the inner surface of the socket 44. The radial slot 78 opens through a peripheral outlet 80 in the sidewall 76 of the body 72. The geometry of the slot 78 is configured to slidingly pass the lanyard 50 through the opening. The slot 78 may be located at any point along the upper surface 74 of the socket seal 70, depending on the shape of the distal aspect of the residual limb 48. As seen in FIGS. 13-15, the slot 78 is configured to receive the plug 68 on the lanyard in a fluid tight sealing relationship. Specifically, as the length of the lanyard 50 is advanced through the slot passage (FIGS. 16 and 17), the plug 68 is forcefully pulled into the slot 78 for sealing the passage and the interior of the socket 44.

A distal socket seal tool may be used as a dummy for fabricating the prosthetic socket 44. The dummy has the same shape as the socket seal 70 to allow for proper fitting by a prosthetist. During fabrication of the socket 44, the dummy is placed on the most distal aspect of a model of a residual limb prior to creating the socket. The socket 44 is then fabricated over the model with the dummy to the shape of the residual limb 48. After fabrication has been completed, the dummy is removed leaving a void within the distal end of the socket 44 having dimensions similar to the socket seal 70. The socket seal 70 is installed into the void created by the dummy. This provides a socket having the proper size and shape to accommodate the socket seal in the final socket. It is understood the socket seal 70 may be affixed to, or molded to, the distal aspect of the prosthetic socket 44 via an appropriate adhesive or mechanical fixation, such as a male or female recess created in the prosthetic socket 44 for allowing the respective embodiments of the socket seal to key into the prosthetic socket.

Figure 18:
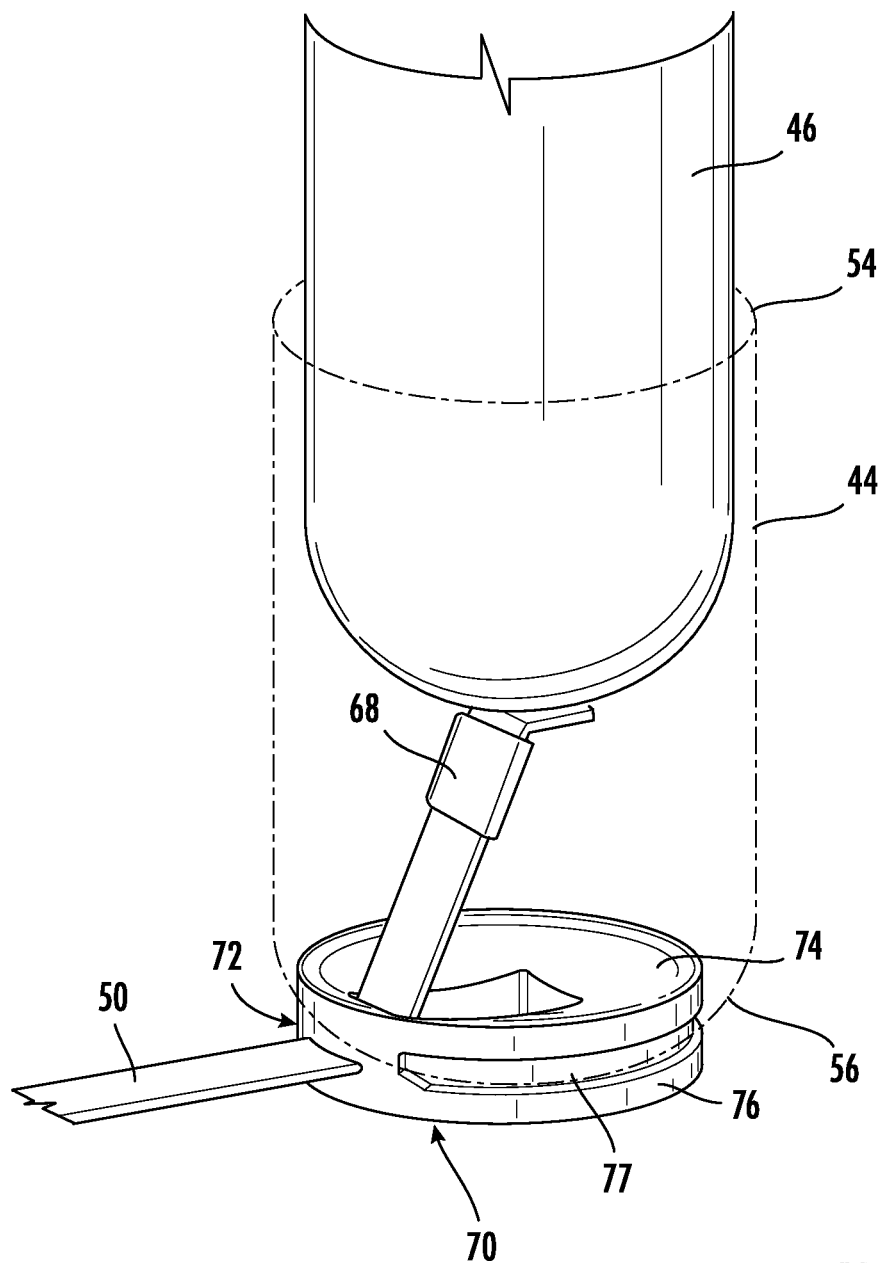
FIG. 18 is a front perspective view of the socket seal and the liner with the lanyard and the sealing element as shown in FIG. 16 and including a prosthetic socket shown in phantom.
Figure 19:
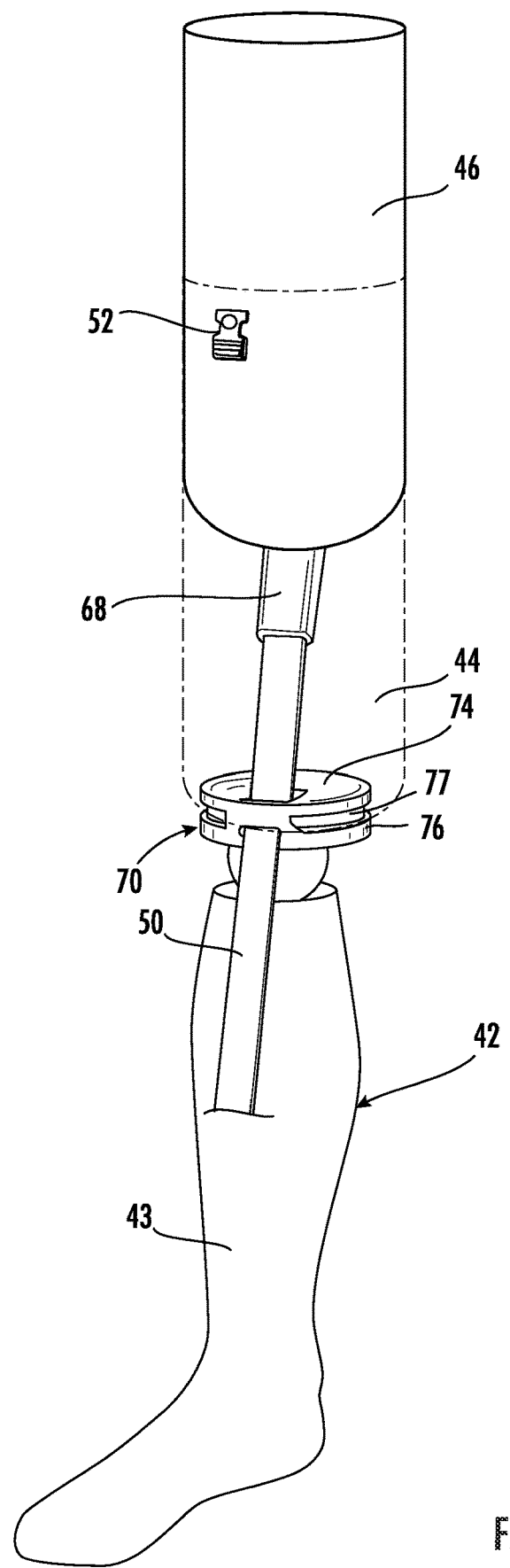
FIG. 19 is a side perspective view of the suspending apparatus and the lower leg prosthesis as shown in FIG. 1 with the prosthesis partially donned.
Figure 20:
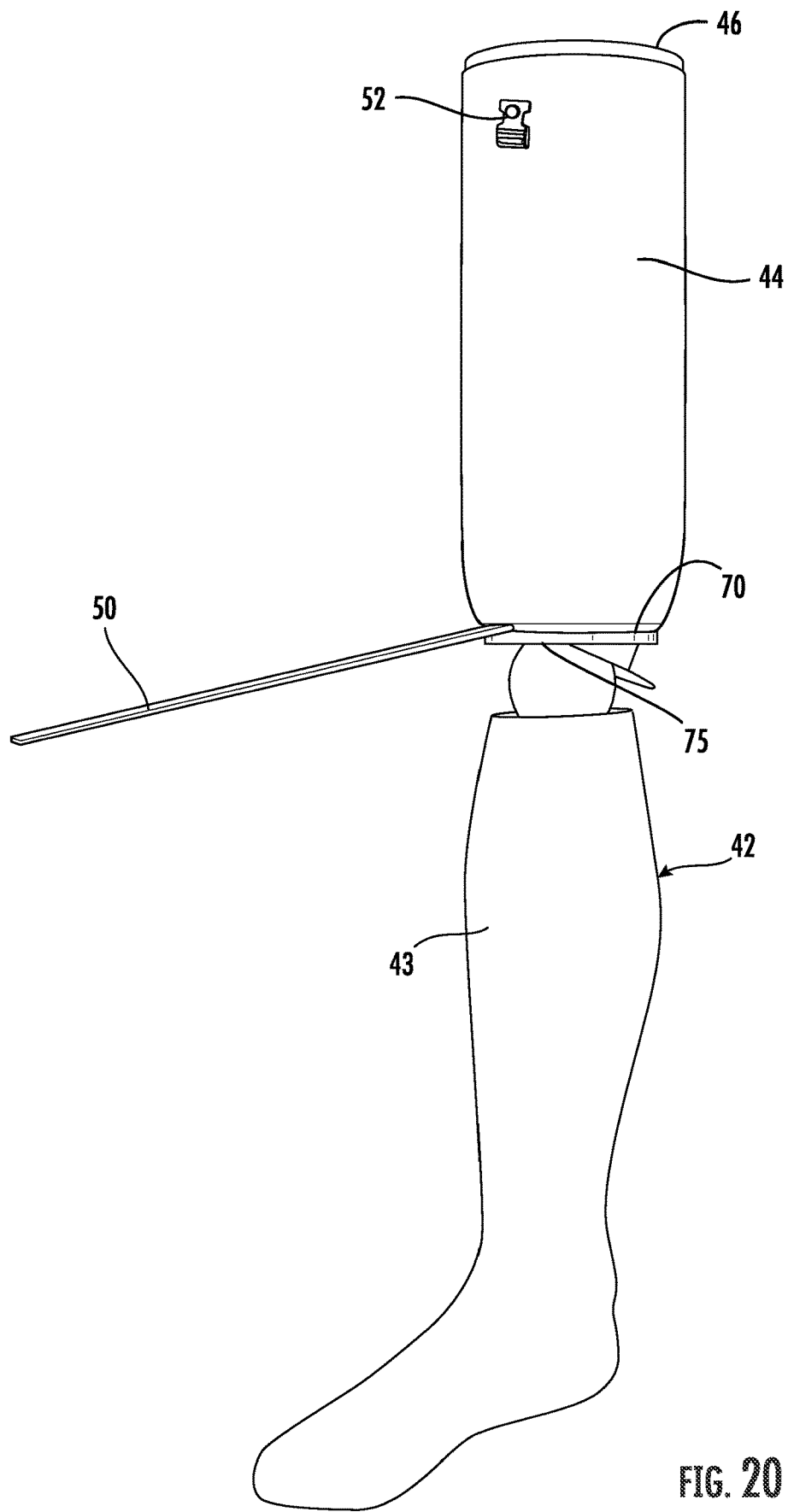
FIG. 20 is a side perspective view of the suspending apparatus and the lower leg prosthesis as shown in FIG. 19 with the prosthesis fully donned.
Figure 21:
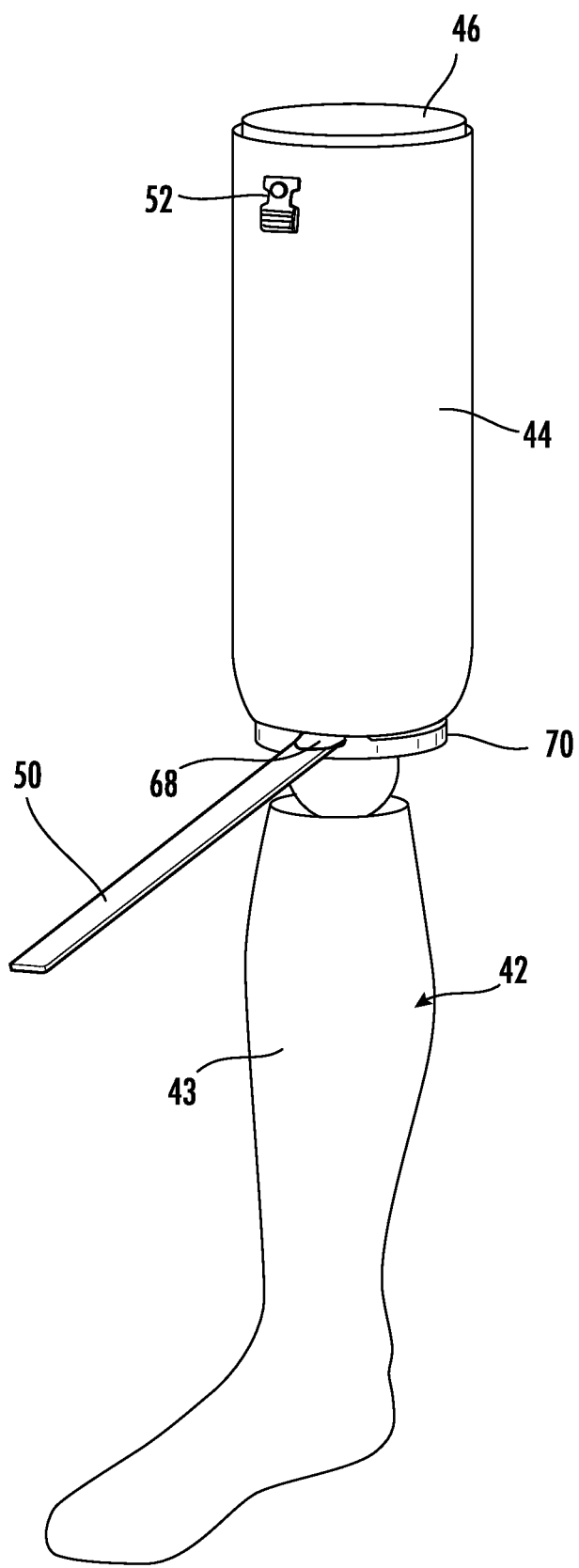
FIG. 21 is a front perspective view of the suspending apparatus and the lower leg prosthesis fully donned as shown in FIG. 20.
Figure 22:
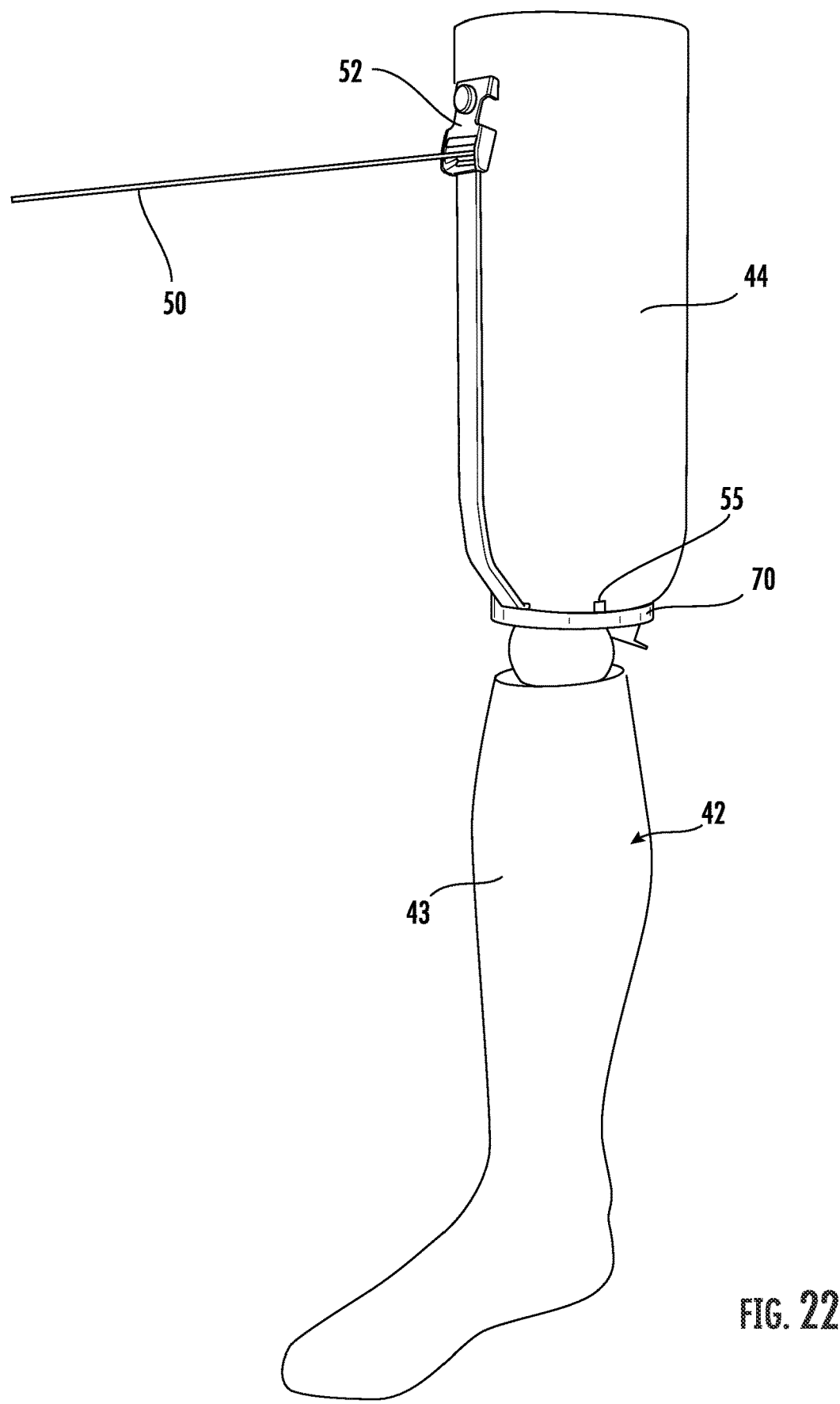
FIG. 22 is a side perspective view of the suspending apparatus and the lower leg prosthesis fully donned as shown in FIG. 20 with the locking mechanism partially secured.
Figure 23:
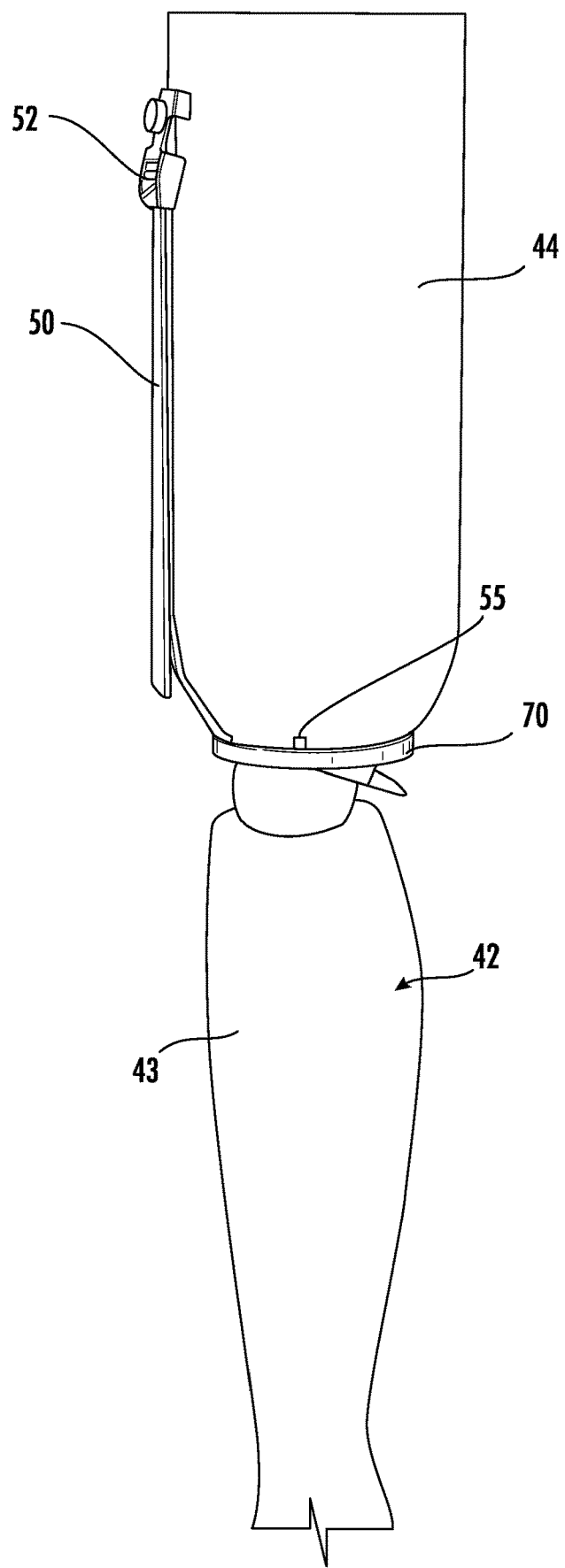
FIGS. 23 and 24 are side and front perspective views, respectively, of the suspending apparatus and the lower leg prosthesis as shown in FIG. 20 with the prosthesis fully donned and the locking mechanism secured.
Figure 24:
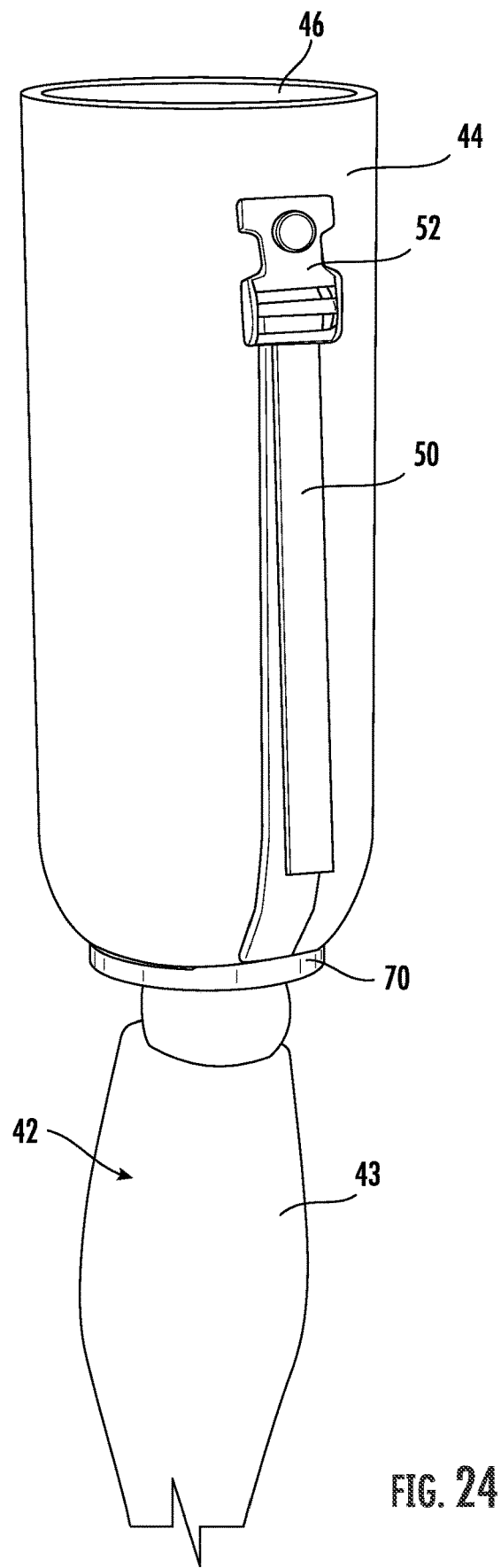

In use, a patient first dons the liner 46 which fits snugly over the residual limb 48. The liner includes the lanyard 50 at the distal end of the liner. The free end of the lanyard 50 is passed through the slot 78 in the socket seal 70. The patient then pushes the residual limb 48 covered with the liner 46 into the socket 44 (FIG. 19). The patient simultaneously pulls the lanyard 50 providing tension necessary to elongate the limb, which further draws the residuum into the socket 44 (FIG. 18). Downward pressure of the residual limb 48 into the socket 44 will force air out through the one-way valve, if present, thereby producing a negative air pressure within socket 44. The liner 46 and the covered residual limb eventually come into contact with the socket seal 70 at the distal end 56 of the socket 44 (FIGS. 20 and 21). When tension on the liner is released, the length of the liner 46 contacts the inner surface of the socket 44 forming an airtight seal between the two surfaces. As described above, the airtight seal around the residual limb 48 within the socket 44 provides negative pressure as a second means of suspension. Referring to FIGS. 22-24, once the socket 44 is completely donned, the lanyard 50 is anchored to the latch 52 on the outer surface of the socket 44, which provides a mechanical lock as a first means of suspension.

The suspension apparatus and system combines the attributes of both the mechanical lanyard suspension and the negative pressure suction suspension of a prosthesis. The prosthesis will not rotate on the residual limb. Manually locking the lanyard on the socket for mechanical suspension safeguards against catastrophic failure in the event of suction loss. The apparatus and system provide many other advantages, including ease of donning with the lanyard placing the limb under tension causing the limb to elongate. This can reduce the time and energy it takes to insert and completely don the prosthesis. Once the residual limb is pulled into the prosthesis, there is visual and audible confirmation that the prosthesis is fully and properly donned because the lanyard locks into a designated position.

The suspension apparatus and system is described and shown herein is for a lower limb above knee prosthesis. It will be understood, however, that the teachings of the suspension apparatus are also applicable for other applications. For example, in one alternative application, the apparatus may be used for a below the knee lower extremity prosthetic limb. Thus, the apparatus and system may be used for any suitable prosthetic limb, including upper extremity prosthetics. Other applications will be apparent to those of ordinary skill in the art.

Although the suspending apparatus, system and method has been shown and described in considerable detail with respect to only a few exemplary embodiments thereof, it should be understood by those skilled in the art that we do not intend to limit ourselves to the embodiments since various modifications, omissions and additions may be made to the disclosed embodiments without materially departing from the novel teachings and advantages of the apparatus, particularly in light of the foregoing teachings. Accordingly, we intend to cover all such modifications, omission, additions and equivalents as may be included within the spirit and scope of the apparatus, system and method as defined by the following claims. In the claims, means-plus-function clauses are intended to sticker the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures.

What is claimed is:

1. An apparatus for suspending a prosthesis from a residual limb having a distal end, the suspending apparatus comprising:
   a tubular flexible resilient liner having a closed distal end, the liner capable of receiving at least a portion of the residual limb including the distal end of the residual limb;
   a lanyard having an end secured to the distal end of the liner and a free end;
   a rigid hollow prosthetic socket having an open proximal end, a closed distal end, and interior side surfaces defining a well capable of
   receiving the residual limb, the prosthetic socket including a socket seal disposed at the distal end of the socket, the socket seal comprising
   a body having an upper surface, a lower surface, and a side wall interconnecting the upper surface and the lower surface,
   wherein the upper surface defines a recess opening through the side wall to the exterior of the socket for forming a passage rectilinear in cross-section for passing the free end of the lanyard; and
   a sealing element disposed along the length of the lanyard, the sealing element comprising a flexible resilient wedge configured to engage the socket seal within the passage,
wherein the free end of the lanyard is pulled through the passage such that the sealing element sealingly engages the socket seal within the passage for preventing fluid communication through the passage between the interior of the socket and exterior of the socket, and
wherein the distal end of the residual limb covered by the liner fits snugly within the socket such that the liner at least partially contacts the interior side surfaces of the socket for providing a fluid seal to the socket and creating negative pressure within the socket.

2. The suspending apparatus of claim 1, wherein the liner comprises a mechanical locking pin configured to engage the one end of the lanyard.

3. The suspending apparatus of claim 2, wherein the locking pin comprises a threaded bolt and nut combination.

4. The suspending apparatus of claim 1, wherein the upper surface of the body of the socket seal is concave.

5. The suspending apparatus of claim 1, wherein the body of the socket seal comprises an elastomer.

6. The suspending apparatus of claim 1, wherein the socket further comprises a one-way valve disposed in a second fluid passage extending through the socket allowing fluid flow only from the interior of the socket to the exterior of the socket and preventing backflow of fluid, wherein as the socket is donned the portion of the residual limb received by the liner forces air from the interior of the socket through the one-way valve to the exterior of the socket for creating negative pressure between the liner and the interior of the socket.

7. The suspending apparatus of claim 1, further comprising a locking mechanism disposed on the exterior surface of the socket, wherein the locking mechanism secures the free end of the lanyard.

8. The suspending apparatus of claim 1, wherein the socket seal is substantially cylindrical.

9. The suspending apparatus of claim 1, wherein the side wall includes an integral radially extending annular flange integrally molded with the socket.

10. The suspending apparatus of claim 1, wherein sidewall of the socket seal defines a circumferential groove.

11. The suspending apparatus of claim 1, further comprising an O-ring seal on the interior side surface adjacent the proximal end of the socket.

12. A prosthesis for a residual limb, the prosthesis comprising:
   a prosthetic socket having an open proximal end, a closed distal end and interior side surfaces defining a well capable of receiving the residual limb;
   a liner disposed in the well and capable of receiving and providing total contact between the residual limb and the interior side surfaces of the prosthetic socket;
   a lanyard depending from a distal end of the liner, the lanyard including an integral sealing element comprising a flexible resilient wedge;
   a socket seal at the distal end of the socket, the socket seal having a proximal upper surface, a distal lower surface, and a side wall interconnecting the upper surface and the lower surface, the upper surface defining a recess opening to the exterior of the socket through the side wall for forming a passage having a rectilinear cross-section for passing the free end of the lanyard such that the sealing element fluidically seals the passage within the socket seal; and
   an artificial limb configured to attach to the socket.

13. A method for suspending a prosthesis from a residual limb having a distal end, the prosthesis suspending method comprising the steps of:
   providing a tubular flexible resilient liner having a closed distal end, the liner including a lanyard having an integral flexible resilient wedge-shaped sealing element and an end secured to the distal end of the liner;
   inserting at least a portion of the residual limb including the distal end of the residual limb into the liner;
   providing a rigid hollow prosthetic socket having an open proximal end, a closed distal end, and interior side surfaces defining a well configured to receive the residual limb, the prosthetic socket including a socket seal disposed at the distal end of the socket, the socket seal comprising a body having an upper surface, a lower surface, and a side wall interconnecting the upper surface and the lower surface, wherein the upper surface defines a recess opening to the exterior of the socket through the side wall for forming a rectilinear passage;
   pulling a free end of the lanyard through the passage for elongating the liner and the residual limb;
   advancing the liner and the elongated residual limb into the socket until the distal end of the residual limb seats against the upper surface of the socket seal and the sealing element engages in the passage within the socket seal for preventing fluid communication through the passage between the interior of the socket and exterior of the socket;
   providing a locking mechanism disposed on the exterior surface of the socket; and
   securing the free end of the lanyard to the locking mechanism.

* * * * *